(12) United States Patent
Van Remmen

(10) Patent No.: US 6,685,890 B1
(45) Date of Patent: Feb. 3, 2004

(54) SHOWER HEAD PROVIDED WITH AN ULTRAVIOLET LAMP

(76) Inventor: Antonius Van Remmen, Postbus 477, 7400 Al Deventer (NL)

( * ) Notice: Subject to any disclaimer, the term of this patent is extended or adjusted under 35 U.S.C. 154(b) by 0 days.

(21) Appl. No.: 09/926,773
(22) PCT Filed: Jun. 15, 2000
(86) PCT No.: PCT/NL00/00412

§ 371 (c)(1),
(2), (4) Date: Dec. 18, 2001

(87) PCT Pub. No.: WO00/78366
PCT Pub. Date: Dec. 28, 2000

(30) Foreign Application Priority Data

Jun. 18, 1999 (NL) .............................................. 1012389

(51) Int. Cl.7 ................................................. B01J 19/08
(52) U.S. Cl. .................................................... 422/186.3
(58) Field of Search ...................................... 422/186.3

(56) References Cited

U.S. PATENT DOCUMENTS 5,891,329 A * 4/1999 Assholder ................... 210/100

FOREIGN PATENT DOCUMENTS

| WO | WO 95/29300 | * 11/1995 |
| WO | WO 97/33631 | * 9/1997 |

* cited by examiner

Primary Examiner—Kishor Mayekar
(74) Attorney, Agent, or Firm—Oblon, Spivak, McClelland, Maier & Neustadt, P.C.

(57) ABSTRACT

An arrangement for irradiating a liquid with ultraviolet radiation. The arrangement includes a low-pressure mercury lamp placed inside a hermetically sealed housing. In addition, inside the housing a converter or a transformer is provided such that the arrangement may operate from a safe, low supply voltage. The housing further includes a humidity sensor, which switches off the supply voltage as soon as a crack or another leak is detected in the housing. The arrangement may advantageously be incorporated into a shower head or another sanitary provision, when a complete sterilization of the supplied water is desirable.

10 Claims, 3 Drawing Sheets

SHOWER HEAD PROVIDED WITH AN ULTRAVIOLET LAMP

TITLE OF THE INVENTION

Figure 1:
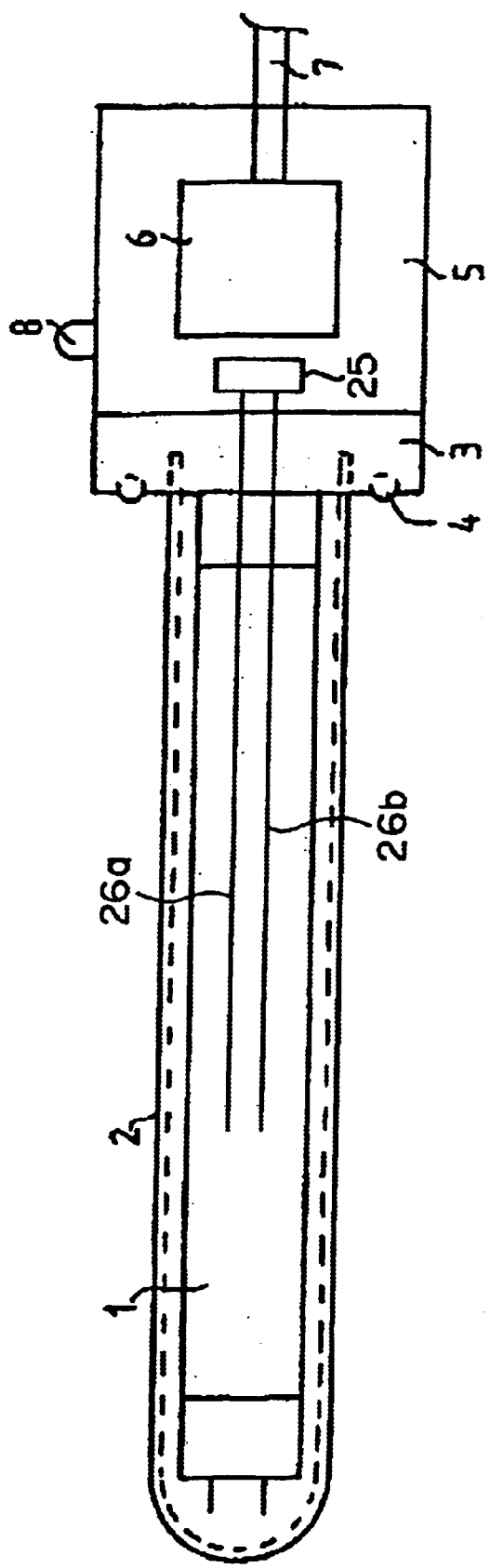

This application is 35 U.S.C. 371 National Stage filing of PCT/WO00/00412 filed Jun. 15, 2000.

BACKGROUND OF THE INVENTION

1. Field of the Invention

The invention relates to an arrangement for irradiating a liquid with ultraviolet radiation, for controlling microorganisms in the liquid, comprising an enclosure of which at least part of a wall is at least partially transparent to ultraviolet radiation, provided with a gas discharge lamp, contained in the enclosure, and connecting means for connecting a supply voltage.

2. State of the Art

Arrangements of this kind are known in the art. They are used for the sterilisation of water and other liquids, for example in the food industry. The disadvantage of the known arrangements is that the supply voltages used are relatively high, which has been considered unavoidable until now, because a working voltage of a gas discharge tube is unavoidably high. The present arrangement obviates this drawback to a large extent and is according to an aspect of the invention characterized in that the enclosure moreover contains a converter or a transformer for transforming the supply voltage to a working voltage for the gas discharge lamp. The undeniable advantage is that the relatively high working voltage is present now only inside the enclosure.

SUMMARY OF THE INVENTION

A favourable embodiment according to an aspect of the invention is characterized in that the enclosure moreover contains a humidity sensor, arranged for switching off the supply voltage or the converter in case of leak or fracture, as a result of which the high voltage disappears in a split second and any safety risk is excluded.

A favourable application is according to another aspect of the invention characterized in that the arrangement forms part of a shower head. In this way, the Legionella problem is specifically addressed. It is well known that ultraviolet radiation effectively controls this bacterium. The present invention enables the water to be disinfected including the water that remains behind in the hose or shower head.

A favorable embodiment of the invention is characterized in that the shower head comprises a handle part and a head part and that the arrangement is coupled to the handle part and to the head part. It is possible then to use a relatively long gas discharge tube, which results in a long irradiation time for the water that flows in from the handle part side, while water that remains behind inside the shower head will be disinfected too.

A favourable embodiment of the inventive shower head is characterized in that the transparent part of the wall separates the shower head in two parts, such that one part is arranged for leading through water and the other part forms the actual enclosure. A favourable embodiment is characterized in that the transparent part is at least substantially flat or slightly convex. A further favourable embodiment is characterized in that at least part of the enclosure has a cross section which is of an at least substantially parabolic shape and is provided with a reflective layer, such that the water will be irradiated uniformly by substantially all ultraviolet radiation emitted by the lamp.

An alternative embodiment of the inventive shower head is characterized in that the transparent part is at least substantially tubular. A favourable embodiment is characterized in that the enclosure comprises an at least for ultraviolet light partly transparent tube, which is closed on one end and coupled to a housing on the other end, in which coupled housing the converter or transformer is housed. In this way, the enclosure becomes a module that can easily be installed or removed.

The invention also relates to a sanitary installation provided with an outlet, via which water becomes available for use, which outlet is provided with an inventive arrangement for irradiating the water. One may think of baths, Jacuzzi baths, saunas, steam baths, therapeutic baths, fountains and the like, where a contamination with the Legionella bacterium is imaginable.

BRIEF DESCRIPTION OF THE INVENTION

Figure 2:
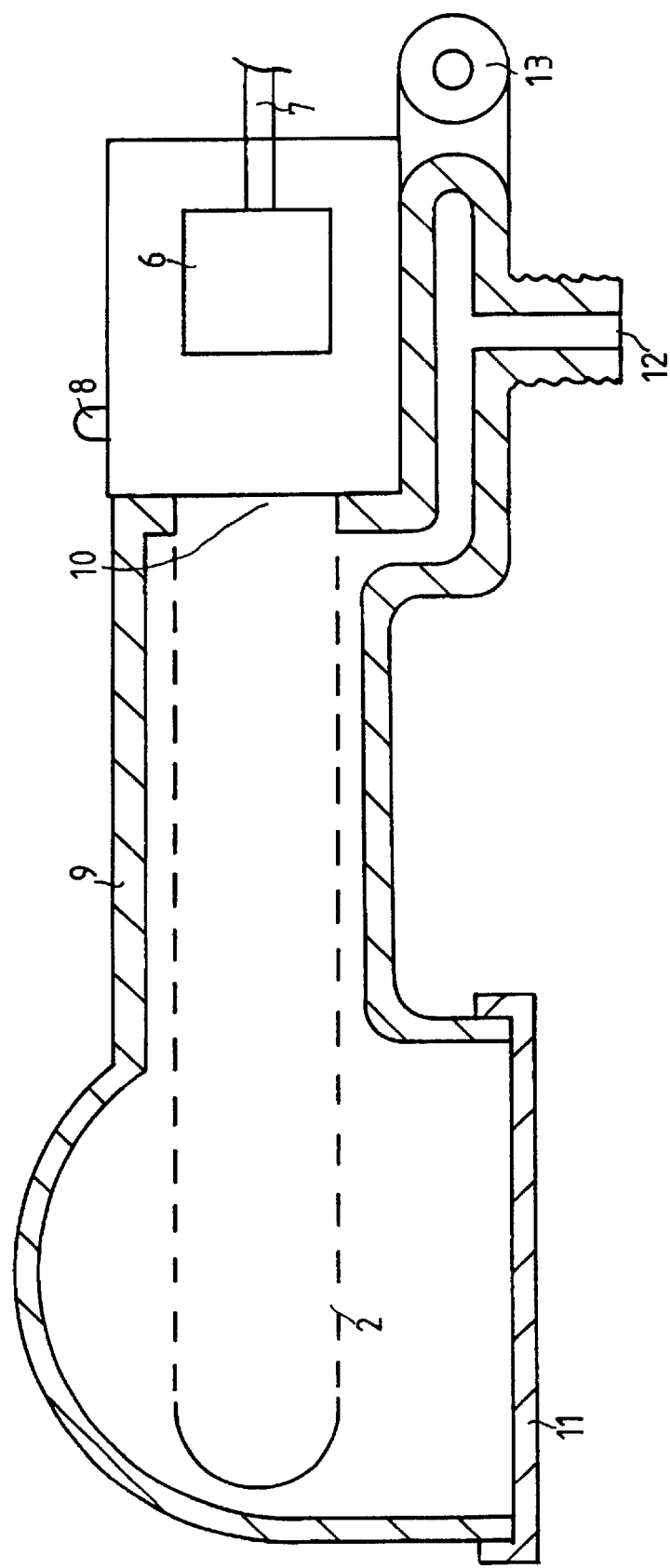
Figure 3B:
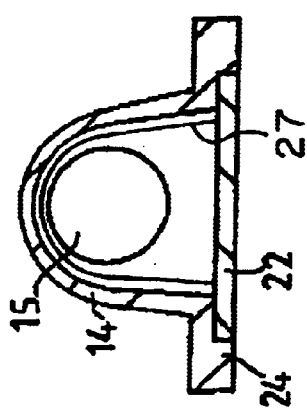
Figure 3A:
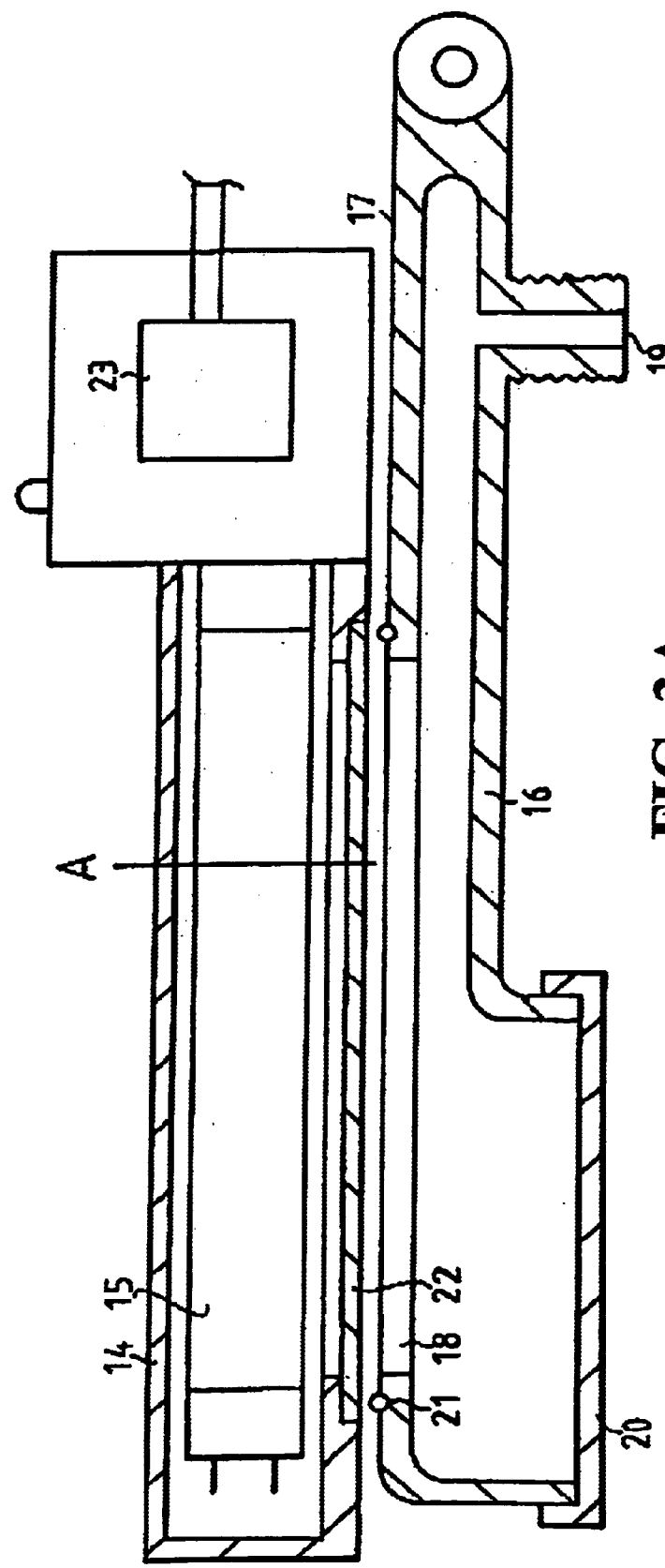

The invention will now be further explained with reference to the following figures, in wich:

FIG. 1 schematically shows a possible embodiment of a modular arrangement, operating on a low supply voltage;

FIG. 2 schematically shows, in a longitudinal section, a possible embodiment of a shower head provided with this arrangement;

FIG. 3A schematically shows, in a longitudinal section, a possible embodiment of a shower head provided with an alternative arrangement;

FIG. 3B schematically shows this alternative arrangement in a cross section.

DETAILED DESCRIPTION OF THE INVENTION

FIG. 1 schematically shows a possible embodiment of a modular arrangement, operating on a low supply voltage, comprising a low pressure gas discharge tube 1 of the fluorescent type, mounted inside a quartz tube 2, which is closed on one side and which is bonded to a cover 3 on the other, open side. Cover 3 is provided with a groove, which contains an O-ring 4. Cover 3 moreover forms part of a housing 5, which housing 5 contains a converter or transformer 6, which receives a supply voltage of 12 volt via a cable 7 and transforms this voltage to a voltage suitable for lamp 1. Suitable transformers or converters are well known in the art; converters are for example found in electric torches provided with a fluorescent lamp. These known converters usually comprise a free running oscillator, which generates an alternating voltage, which alternating voltage is next transformed to an alternating voltage in the order of three hundred volt. With this voltage, lamp 1 easily ignites, without the filaments in the lamp being heated. Moreover, the arrangement is provided with a humidity sensor located inside housing 5, comprising a comparator 25, well known in the field, arranged for measuring a voltage between two separated bare wires 26a, 26b, situated inside tube 2. The wires are connected to two different voltages via resistors having a high resistance. When moisture enters tube 2, an electric leak will form between the two wires and the voltage difference will decrease. This is measured by the comparator 25 and the free running oscillator is switched off in a manner well known in the art or the supply voltage is interrupted, as a result of which the relatively high working voltage for lamp 1 is switched off in a split second. In this manner, safety risks are entirely excluded. For testing the well functioning of the arrangement, housing 5 is provided with a green-coloured LED 8 which lights up when converter or transformer 6 functions well and the current supplied to lamp 1 is within previously determined values.

FIG. 2 schematically shows, in a longitudinal section, a possible embodiment of a shower head 9 provided with the inventive arrangement, in which tube 2 protrudes into shower head 9 via an opening 10 up to the spray nozzle 11 and in which water, supplied via a supply nipple 12, is fed alongside tube 2 for obtaining a relatively long exposure time. When the arrangement is switched on before the water starts running, then only irradiated water is supplied and there is no hidden volume in which the Legionella bacterium or other organisms may develop and be released when the shower is used. Shower head 9 can be rotatably mounted in the usual manner with the aid of a flange 13, but it may also be used as a hand shower, in which case the safety is guaranteed by the low supply voltage which is supplied via cable 7. Cable 7 ends in a drip-proof recessed connecting box, well known in the art, in which a transformer is located for transforming the mains voltage to for example 12 volt.

It is also possible to guide cable 7 via supply nipple 12, in which case a T-piece must be incorporated in the water mains for separating cable 7 from the water mains.

In a fully analogous manner, the arrangement may be built-in in a cock for a bath or in a similar water outlet for which it is considered desirable to control the Legionella bacterium.

FIG. 3A schematically shows, in a longitudinal section, a possible embodiment of a shower head provided with an alternative arrangement according to the invention, in which a housing 14, containing a gas discharge lamp 15, is shown separated from a shower head 16 for the sake of clearness. Shower head 16 is provided with a flat upper side 17, in which lengthwise a slot 18 is made, via which ultraviolet radiation can irradiate the water that is supplied via a supply nipple 19 and that is delivered to a spray nozzle 20. Around slot 18 an O-ring 21 is placed and housing 14 is fastened to the upper side 17 of shower head 16, in such a way that a quartz window 22 in co-operation with O-ring 21 seals off slot 18. Lamp 15 is connected to a converter or transformer 23, provided with a humidity sensor, operating in a similar manner as the arrangement described with reference to FIG. 1.

FIG. 3B schematically shows this alternative arrangement in a cross section according to line A in FIG. 3A, with housing 14, lamp 15 and window 22. In cross section, housing 14 is of an at least substantially parabolic shape and its inside has been polished or is provided with a metallic layer 27, such that substantially all ultraviolet radiation emitted by lamp 15 is transferred to the water via window 22 and slot 18. Housing 14 is moreover provided with a flange 24, surrounding window 22, in which holes have been drilled, not shown in the figure, which holes correspond with blind, threaded holes in upper side 17, for fastening housing 14 with screws onto shower head 16.

What is claimed is:

1. Arrangement for irradiating a liquid with ultraviolet radiation, and for controlling micro-organisms in the liquid, comprising an enclosure of which at least part of a wall is at least partially transparent to ultraviolet radiation; a gas discharge lamp, contained in the enclosure; connecting means for connecting a supply voltage, wherein the enclosure moreover contains a converter or a transformer for transforming the supply voltage to a working voltage for the gas discharge lamp; and a humidity sensor, arranged for switching off the supply voltage or the converter in case of leak or fracture.

2. Shower head, provided with an arrangement as claimed in claim 1.

3. Shower head according to claim 2, wherein the shower head comprises a handle part and a head part and that the arrangement is coupled to the handle part and to the head part.

4. Shower head according to claim 3, wherein the transparent part of the wall separates the shower head in two parts, such that one part is arranged for leading through water and the other part forms the actual enclosure.

5. Shower head according to claim 4, wherein the transparent part is at least substantially flat or slightly convex.

6. Shower head according to claim 5, wherein at least part of the enclosure has a cross section which is of an at least substantially parabolic shape and is provided with a metallic layer to reflect the ultraviolet radiation.

7. Shower head according to claim 4, wherein the transparent part is at least substantially tubular.

8. Shower head according to claim 7, wherein at least part of the enclosure comprises an ultraviolet light partly transparent tube, which is closed on one end and coupled to a housing on the other end, where the converter or transformer is housed.

9. Sanitary installation provided with an outlet, via which water becomes available for use, wherein in the outlet an arrangement according to claim 1 has been integrated.

10. Sanitary installation provided with an outlet, via which water becomes available for use, wherein in the outlet an arrangement according to claim 1 has been integrated.

* * * * *